United States Patent [19]

Malloy et al.

[11] Patent Number: 4,499,300

[45] Date of Patent: Feb. 12, 1985

[54] 4-VINYLBENZENEACETIC ACID

[75] Inventors: Thomas P. Malloy, Lake Zurich; Dusan J. Engel, Des Plaines, both of Ill.

[73] Assignee: UOP Inc., Des Plaines, Ill.

[21] Appl. No.: 566,007

[22] Filed: Dec. 27, 1983

[51] Int. Cl.$^3$ ............................................. C07C 63/64
[52] U.S. Cl. .................................... 562/495; 568/308; 562/493; 562/413
[58] Field of Search ................................ 562/495, 413

[56] References Cited

U.S. PATENT DOCUMENTS 4,362,891 12/1982 Guerrato et al. .................... 562/495

Primary Examiner—Paul J. Killos
Attorney, Agent, or Firm—William H. Page, II; Eugene I. Snyder

[57] ABSTRACT

A multi-step preparation of 4-vinylbenzeneacetic acid from the readily available 1,4-diethylbenzene is described. The method uses cobalt (II) catalyzed oxidation of 1,4-diethylbenzene to 4-ethylacetophenone followed by oxidative rearrangement of the latter to 4-ethylbenzeneacetic acid, selective photochlorination to produce 4-(1'-chloroethyl)benzeneacetic acid, and finally base-catalyzed dehydrochlorination of the latter to afford the title compound.

8 Claims, No Drawings

4-VINYLBENZENEACETIC ACID

BACKGROUND OF THE INVENTION

The title compound, 4-vinylbenzeneacetic acid, is a monomer which finds potential as a copolymer with, for example, styrene. The resulting materials may be used as plasticizers, ion exchange resins, and so on. The monomer itself also may be valuable in adhesive formulations. However, applications development has been hindered by the material's limited supply. In particular, there presently is no adequate synthesis utilizing commercially accessible precursors.

The purpose of our invention is to provide a synthetic route to 4-vinylbenzeneacetic acid from 1,4-diethylbenzene, a relatively available material of commerce. The synthesis involves the initial selective oxidation of 1,4-diethylbenzene to 4-ethylacetophenone, oxidatively rearranging the latter to 4-ethylbenzeneacetic acid, selectively monochlorinating the latter acid at the benzylic carbon of the ethyl group, followed by base-catalyzed dehydrochlorination of the resulting 4-(1'-chloroethyl)benzeneacetic acid to 4-vinylbenzeneacetic acid, and recovering the latter.

The initial stage in our preparative route involves the oxidation of 1,4-diethylbenzene with oxygen in the presence of cobalt (II) compounds. Such oxidations typically are performed in air, although oxygen may be substituted therefor, at pressures ranging from atmospheric up to about 100 psig. Oxidation temperatures usually run between about 80° and 140° C., with a narrower range of from about 90° to about 120° C. being preferred.

Among the cobalt (II) compounds which may be used as catalysts for this oxidation are included cobalt phthalocyanine, cobalt salts of carboxylic acids, and cobalt salts of sulfonic acids. Among the carboxylic acids whose salts may be used are included acetylacetic acid, the alkanecarboxylic acids containing from about 8 to about 18 carbon atoms, and naphthalenecarboxylic acid, with the latter being particularly useful. Among the alkanecarboxylic acids whose cobalt salts may be used as catalysts may be mentioned octanoic, nonanoic, decanoic, undecanoic, dodecanoic, tridecanoic, tetradecanoic, pentadecanoic, hexadecanoic, heptadecanoic, and octadecanoic acids. Among the sulfonic acids whose cobalt salts are frequently employed may be mentioned benzenesulfonic acid, toluenesulfonic acid, and methanesulfonic acid, with the toluenesulfonate salt finding broadest use.

In the aforementioned oxidation one methylene group of 1,4-diethylbenzene is transformed into a carbonyl group to afford as the product 4-ethylacetophenone. This latter compound is then oxidatively rearranged by the Kindler modification of the Willgerodt reaction. In this reaction, the ketone is heated with sulfur and an amine, the resulting intermediate is hydrolyzed with base, and after acidification there is obtained the resulting 4-ethylbenzeneacetic acid.

Generally both sulfur and the amine are used in approximately the same molar proportion, with from about 1 to about 8, preferably from about 2 to about 4, molar proportions of each, relative to 4-ethylacetophenone. Among the amines which may be employed morpholine is especially advantageous, as are alkyl-substituted pyridines, e.g., the lutidines and collidines, and the picolines. However, it is to be understood that a wide variety of other tertiary amines may be employed, although not necessarily with equivalent results. The reaction is conducted at a temperature from about 100° to about 150° C., more particularly between about 115° and 135° C. It has been found that removal of water during the heating period is beneficial. Reaction times typically are from about 1 to about 5 hours, depending upon the temperature employed.

After reaction with sulfur and the tertiary amine is complete the resulting intermediate is hydrolyzed with alkali. Aqueous solutions of the alkali metal hydroxides are most conveniently employed, although other alkaline materials, such as the alkali metal carbonates, may be used without prejudice. Typically, a large excess of a relatively strong (10–30%) solution of alkali is employed with hydrolysis being conducted at about 100° C. for a time between about 5 and about 15 hours. After base hydrolysis the reaction mixture is acidified, generally with any mineral acid, to liberate the free acid and unreacted sulfur. Sulfur is readily removed from the organic acid mixture by treatment with base, for example, sodium bicarbonate, which dissolves the organic acid selectively.

The next step in the preparation is photochlorination of 4-ethylbenzeneacetic acid using ultraviolet irradiation with between about 1 and 2 molar proportions of chlorine. Chlorination is continued to about 50% conversion in order to maximize selectivity of monochlorination. Typically, photochlorination is conducted in an ultraviolet transparent solvent, itself not chlorinated under reaction conditions, with chlorinated alkanes, such as carbon tetrachloride, chloroform, methylene chloride, hexachloroethane, and so on, being commonly used. Photochlorination may be conducted at a temperature between about 20° and about 80° C., even more usually between about 35° and about 65° C.

The last stage in our preparative sequence involves dehydrochlorination of 4-(1'-chloroethyl)benzeneacetic acid with an alkali metal hydroxide or alkoxide. Among the hydroxides sodium hydroxide and potassium hydroxide are preferred. Among the alkoxides the sodium, potassium, and lithium salts of primary and secondary alcohols containing up to about 6 carbons are most usually employed. Examples include such alkoxides as sodium methoxide, potassium methoxide, lithium methoxide, potassium ethoxide, sodium propoxide, lithium butoxide, sodium pentoxide, and sodium hexoxide. Solutions of the base may vary between about 5% and about 20% and the reaction is effected between about 25° and about 80° C. The title compound, 4-vinylbenzeneacetic acid, then is isolated from the reaction mixture as by acidification followed by extraction.

The following examples are merely illustrative of this invention and are not intended to limit it thereby.

EXAMPLE 1

Oxidation of 1,4-Diethylbenzene

Oxidations were performed in a 50 ml flask fitted with a bottom-sealed sintered disc to effect air dispersion, a condenser, and a Dean-Stark trap. The flask was charged with 10 grams of 1,4-diethylbenzene while air flowed through the sintered disc at a rate between 125 and 250 cc per minute. The cobalt compound used as a catalyst was added, and the contents heated to the desired temperature. Samples were withdrawn periodically and analyzed by gas-liquid chromatography to afford the results summarized in Table 1. The product, 4-ethyl acetophenone, was then isolated by the fractional vacuum distillation of the oxidation product mixture prior to its use as a reactant in the next step of our synthetic scheme.

TABLE 1

Air Oxidation of 1,4-Diethylbenzene

| Catalyst, Amount, mol % | T°C. | P, psig | Time, h | Conv. % | Selectivity, %, to 4-ethyl-acetophenone |
|---|---|---|---|---|---|
| Co (acetylacetate)$_2$ 0,19 | 105–110 | Atm. | 6 | 38 | 61 |
|  |  |  | 16 | 68 | 63 |
| Co (neo-decanoate)$_2$ 0.19 | 110–115 | Atm. | 6 | 49 | 83 |
| Co (stearate)$_2$ 0.19 | 110–115 | Atm. | 9.5 | 73 | 79 |
| Co (naphthenate)$_2$ 0.26 | 120 | Atm. | 6 | 78 | 72 |
|  |  |  | 7 | 80 | 68 |
| Co (toluenesulfonate)$_2$ 3.00 | 90 | Atm. | 4 | 94 | 44 |
| Co (toluenesulfonate)$_2$ 3.00 | 120 | Atm. | 2 | 0 | 0 |
| Co phthalocyanine 0.26 | 120 | Atm. | 2 | 26 | 81 |
|  |  |  | 5 | 26 | 81 |

EXAMPLE 2

Preparation of 4-Ethylbenzeneacetic Acid

A 300 ml 3-neck flask equipped with a mechanical stirrer, condenser, dropping funnel, and Dean-Stark trap was charged with 66.9 grams (0.45 mol) 4-ethylacetophenone, 62.1 grams (0.71 mol) morpholine, and 22.8 grams (0.71 mol) sulfur. The contents were heated to 135°–140° C. under nitrogen, in some cases with removal of water. After 3 hours, the mixture was cooled to about 40° C. and about 120 grams of a 20% aqueous sodium hydroxide solution was added with stirring. This mixture was then heated to reflux and stirred for about 9 hours. After the reaction mixture was cooled some of the morpholine and water were distilled off at 90–100 Torr. To the residue at 60° C. was added slowly with stirring 50 ml of concentrated hydrochloric acid brought to boiling and the hot reaction mass was stirred for about 1 hour. The solid, which is a mixture mainly of the formed acid and sulfur, was collected after cooling by filtration and subsequently extracted with a 15% aqueous solution of sodium bicarbonate. The filtrate then was heated to boiling, decolorized with carbon, filtered, and the procedure repeated with the filtrate. The solid was washed with hot water, and the combined filtrates were acidified with concentrated hydrochloric acid to precipitate the free 4-ethylbenzeneacetic acid which was collected by filtration. Comparison of experiments performed with and without water removal during the morpholine-sulfur stage is shown in Table 2.

TABLE 2

Effect of H$_2$O Removal

| T°C. | Reaction H$_2$O Removal | Yield 4-Ethyl-benzeneacetic Acid, % | % Recovery Sulfur | Morpholine |
|---|---|---|---|---|
| 113 | No | 65 | 25.7 | 100 |
| 130 | Yes | 72 | 100 | — |

EXAMPLE 3

Preparation of 4-(1'-Chloroethyl)benzeneacetic Acid

A solution of 4-ethylbenzeneacetic acid in either carbon tetrachloride or chloroform was reacted with chlorine while being irradiated with ultraviolet light. Results are summarized in Table 3.

TABLE 3

Synthesis of 4-(1'-Chloroethyl)benzeneacetic Acid

| Expt. | T°C. | Cl$_2$ Added Mole | Solvent | Conversion, %[e] | Selectivity %[e] |
|---|---|---|---|---|---|
| 1[a] | 45 | 0.01 | CCl$_4$ | 50 | 100 |
| 2[b] | 50 | 0.04 | CCl$_4$ | 64 | 80 |
| 3[c] | 40–45 | 0.19 | CHCl$_3$ | 52 | 100 |
| 4[d] | 40–45 | 0.38 | CHCl$_3$ | 92 | 60 |

[a] 0.01 m reactant, 15 mL CCl$_4$, time = 0.33 h
[b] 0.04 m reactant, 70 mL CCl$_4$, time = 0.33 h
[c] 0.183 m reactant, 200 mL CHCl$_3$, time = 1.25 h
[d] Sample 3 continued to be chlorinated with another 0.19 m Cl$_2$
[e] NMR analysis As the results show, selectivity of monochlorination at the benzylic carbon of the ethyl group is quantitative up to about 50% conversion.

EXAMPLE 4

Dehydrochlorination of 4-(1'-Chloroethyl)benzeneacetic Acid

To a solution of 4-(1'-chloroethyl)benzeneacetic acid in methanol may be added about 5 molar proportions of sodium methoxide. The mixture may be stirred with gentle heating (about 50° C.) for several hours. The cooled solution may then be acidified with a slight excess of 5% aqueous hydrochloric acid and extracted with ether to collect 4-vinylbenzeneacetic acid.

What is claimed is:

1. A method of preparing 4-vinylbenzeneacetic acid comprising oxidizing 1,4-diethylbenzene in the presence of cobalt (II) compounds selected from the group consisting of cobalt phthalocyanine, cobalt salts of carboxylic acids, and cobalt salts of sulfonic acids, converting the resulting 4-ethylacetophenone to 4-ethylbenzeneacetic acid using sulfur and morpholine followed by base, photochlorinating the 4-ethylbenzeneacetic acid to 4-(1'-chloroethyl)benzeneacetic acid, dehydrochlorinating said 4-(1'chloroethyl)benzeneacetic acid with a base, and recovering the 4-vinylbenzeneacetic acid formed thereby.

2. The method of claim 1 where the carboxylic acid is selected from the group consisting of acetoacetic acid, alkanecarboxylic acids containing from about 8 to about 18 carbon atoms, and naphthalenecarboxylic acid.

3. The method of claim 2 where the acid is naphthalenecarboxylic acid.

4. The method of claim 1 where the sulfonic acid is selected from the group consisting of benzenesulfonic acid, toluenesulfonic acid, and methanesulfonic acid.

5. The method of claim 4 where the acid is toluenesulfonic acid.

6. The method of claim 1 where the dehydrochlorination is performed using an alkali metal hydroxide or alkoxide as the base.

7. The method of claim 6 where the base is sodium or potassium hydroxide.

8. The method of claim 6 where the base is a sodium or potassium salt of a primary or secondary alcohol containing up to about 6 carbon atoms.

* * * * *